US007925603B1

(12) United States Patent
Laidig et al.

(10) Patent No.: US 7,925,603 B1
(45) Date of Patent: Apr. 12, 2011

(54) SYSTEM FOR MEASURING AND IMPROVING PATIENT FLOW IN HEALTH CARE SYSTEMS

(75) Inventors: William A. Laidig, Madison, AL (US); David M. Klubert, Portland, OR (US)

(73) Assignee: Apogee Informatics Corp., Madison, AL (US)

( * ) Notice: Subject to any disclaimer, the term of this patent is extended or adjusted under 35 U.S.C. 154(b) by 712 days.

(21) Appl. No.: 11/818,175

(22) Filed: Jun. 13, 2007

Related U.S. Application Data

(60) Provisional application No. 60/814,034, filed on Jun. 16, 2006.

(51) Int. Cl.
*G06F 17/00* (2006.01)
*G06N 5/00* (2006.01)
(52) U.S. Cl. ........................................................ 706/45
(58) Field of Classification Search ...................... 706/45
See application file for complete search history.

(56) References Cited

U.S. PATENT DOCUMENTS

2002/0107769 A1* 8/2002 Dashefsky et al. ............. 705/35

OTHER PUBLICATIONS

Michalowski et al. "Mobile clinical support system for pediatric emergencies", Decision Support Systems 36 (2003) 161-176.*
Fernandes et al., "Use of Continuous Quality Improvement to Facilitate Patient Flow Through the Triage and Fast-Track Areas of an Emergency Department", J. of Emergency Medicine, vol. 13, Non 6, 1995, pp. 847-855.*

* cited by examiner

*Primary Examiner* — Donald Sparks
*Assistant Examiner* — Li-Wu Chang
(74) *Attorney, Agent, or Firm* — Young Basile

(57) ABSTRACT

The invention is a software-based method for displaying, analyzing, simulating and optimizing patient flow in a health care facility, including computer hardware for storage of data, as well as software for retrieving data and for creating mathematical models to represent patient treatment and transit within a healthcare facility.

6 Claims, 10 Drawing Sheets

Ready_for_Swope4[Severity_Levels](t) = Ready_for_Swope4[Severity_Levels](t - dt) + (Triaged_Patients_Outflow_4[Severity_Levels] - Swope_Turndown4_Separate[Severity_Levels] - Swope_Accept4_Separate[Severity_Levels]) * dtINIT
Ready_for_Swope4[Severity_Levels] = 0
INFLOWS:
Triaged_Patients_Outflow_4[Severity_Levels] = CONVEYOR OUTFLOW
    TRANSIT TIME =
(NP_Screening_Time+Quick_Registration_Time+Triage_Nurse_Determine_Chief_Complaint)/60
OUTFLOWS:
Swope_Turndown4_Separate[Severity_Levels] = if Sev4declined_Swope / NP_Output_4 < Swope_Turndown_Percentage /100 then SepSpeed2 else 0
Swope_Accept4_Separate[Severity_Levels] = if Sev4Accepted_Swope/ NP_Output_4 < (100-Swope_Turndown_Percentage)/100 then SepSpeed2 else 0
Ready_for_Swope5[Severity_Levels](t) = Ready_for_Swope5[Severity_Levels](t - dt) + (Triaged_Patients_Outflow_5[Severity_Levels] - Swope_Turndown5_Separate[Severity_Levels] - Swope_Accept5_Separate[Severity_Levels]) * dtINIT
Ready_for_Swope5[Severity_Levels] = 0
INFLOWS:
Triaged_Patients_Outflow_5[Severity_Levels] = CONVEYOR OUTFLOW
    TRANSIT TIME =
(NP_Screening_Time+Quick_Registration_Time+Triage_Nurse_Determine_Chief_Complaint)/60
    ARREST IF Arrest_Logic = 1
OUTFLOWS:
Swope_Turndown5_Separate[Severity_Levels] = if Sev5declined_Swope / NP_Output_5 < Swope_Turndown_Percentage/100 then SepSpeed2 else 0
Swope_Accept5_Separate[Severity_Levels] = if Sev5Accepted_Swope /NP_Output_5 < (100 - Swope_Turndown_Percentage)/100 then SepSpeed2 else 0
Reg_Error_Value(t) = Reg_Error_Value(t - dt) + (Reg_Error_Accumulator) * dtINIT
Reg_Error_Value = 0
INFLOWS:
Reg_Error_Accumulator = ABS(Registered_Patient_Error)
Sev4Accepted_Swope(t) = Sev4Accepted_Swope(t - dt) + (Slave3) * dtINIT
Sev4Accepted_Swope = 0
INFLOWS:
Slave3 = Swope_Accept4_Separate[S4]
Sev4declined_Swope(t) = Sev4declined_Swope(t - dt) + (Slave1) * dtINIT
Sev4declined_Swope = 0
INFLOWS:
Slave1 = Swope_Turndown4_Separate[S4]
Sev5Accepted_Swope(t) = Sev5Accepted_Swope(t - dt) + (Slave4) * dtINIT
Sev5Accepted_Swope = 0
INFLOWS:
Slave4 = Swope_Accept5_Separate[S5]
Sev5declined_Swope(t) = Sev5declined_Swope(t - dt) + (Slave2) * dtINIT
Sev5declined_Swope = 0
INFLOWS:
Slave2 = Swope_Turndown5_Separate[S5]

InFlow

| | |
|---|---|
| # Waiting | 5 ↑ |
| Acuity at Triage | 3.0 ↑ |
| LWBS | 1 |
| # Presenting | 24 |

Forecasted Walkins - 2hrs: 6
EMS Patients / Hr: 2
Number in ED from Previous Night: 38

Current Time: 6/13/07 9:17 AM
Last Patient Draw: 6/7/07 9:25 AM
Inst. Screen Update Time: 9:31 PM
Timer Setting: 5 min
Version 0.05

Throughput

| | |
|---|---|
| Current Capacity | 37  9% ↓ |
| Current ED Acuity | 0.0  ↑ |
| Current ED LOS Severity 1 | 0.00 |
| Severity 2 | 0.00 |
| Severity 3 | 0.78 |
| Severity 4 | 1.43 |
| Severity 5 | 0.00 |

Current T&R LOS: 2.08  2.09
Current Admit LOS: 3.02  3.21
ACS Current / Count / LOS: 0  4  1.38
CVA Current / Count / LOS: 0  3
XFR Current / Count / LOS: 2  3
Trauma Current / Count: 0  2
Psych Current / Count: 0  0
SANE Current / Count: 0  0

OutFlow

| | |
|---|---|
| In Patient Holding | 1  6% ↕ |
| Tele Patients | 3 |
| ICU Patients | 0 |
| Med/Surg Patients | 0 |

ED Hold Time: 1.09
Admits: 17
T&R: 40
Leaving AMA: 2
Disposition Rate: 6.2

Switch to Current Day History View

Switch to Graphical Instrument View

Settings
Start Timer
Stop Timer

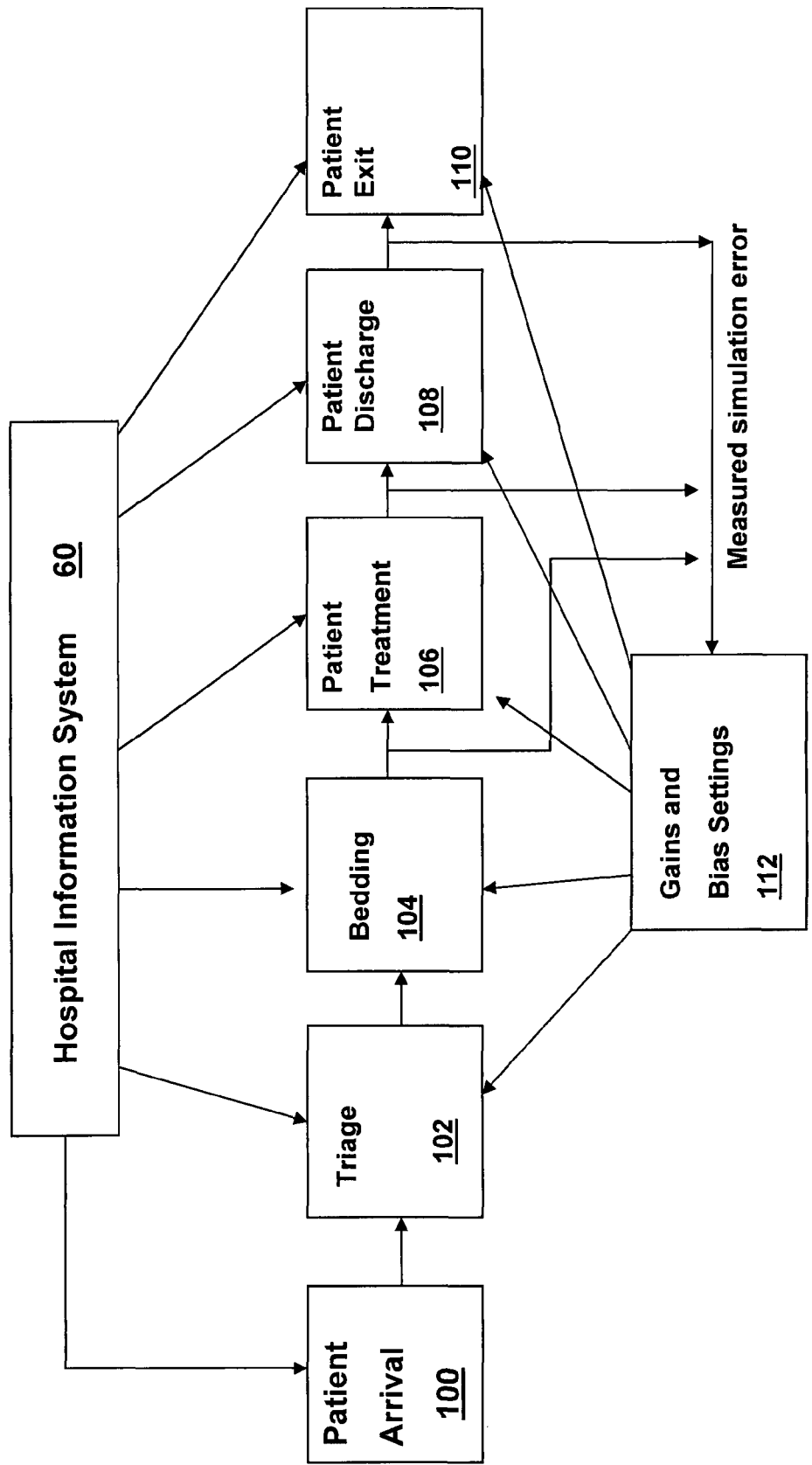

SYSTEM FOR MEASURING AND IMPROVING PATIENT FLOW IN HEALTH CARE SYSTEMS

This application claims the benefit of the filing date of U.S. Provisional Patent Application No. 60/814,034, filed Jun. 16, 2006.

FIELD OF THE INVENTION

The invention pertains to methods for monitoring the flow of patients within a health care system, and more particularly, to methods and apparatus for measurement, displaying, modeling, and forecasting patient flow within health care facilities, such as hospitals, and between and within health care facilities which make up larger health care systems. The invention includes computer-based manipulation of models and simulation of processes within a model to improve model function and optimization of the system being modeled.

BACKGROUND OF THE INVENTION

National health care systems exhibit a wide range of performance inefficiencies. The United States health care system, in particular, is characterized by a high degree of scientific, financial, and managerial complexity. The United States health care system is a complex matrix of health care providers, consumers, payers, and regulators. It is widely recognized that this system is plagued with problems, exhibiting a tendency toward ever-increasing levels of care and cost, even in the absence of measurable benefit. This evolution in the health care system imposes enormous strains and imposes unreasonable expense.

It is currently believed that better health care, in terms of patient outcomes, is obtained by expanded use of health information technology.

With the widespread availability of inexpensive, capable, and networked computer systems, health care facilities are capable of acquiring and maintaining vast amounts of information regarding patients. At each step during the treatment process, data regarding the patient may be collected and stored. In addition to patient identification information, health care facility databases routinely include data regarding a patient's evaluation, diagnosis, treatment, testing, billeting, prognosis, and discharge. Additionally, the acquired data provides information regarding the location and movement of patients to, from, and within the institution. Sharing of information regarding patients and their care is today a widely accepted practice, even a necessity, in the modern health care environment. The use of computer networks to share information regarding patients and their treatment is well known, and a variety of systems have been disclosed, such as those taught by Engleson, et al. in U.S. Pat. No. 7,107,106 and Labounty, et al. in U.S. Pat. No. 6,871,211. These systems can include automated telemetry which allows, for example, real-time monitoring of particular physiological data which is constantly transmitted to and updated within networked databases in hospital environments.

Missing from current technology, however, are methods for analyzing and optimizing the actual flow of patients to, from, and within the treatment environment, e.g., a modern, complex hospital campus.

By evaluating the detailed characteristics of the health care facility, including all of its departments and sub-departments, it is possible to evaluate, simulate, and forecast patient flow, from admission to discharge, to optimize facility utilization and improve cost-effectiveness while improving the overall quality of health care to the patient. The invention, therefore, is designed to effectively measure patient flow, record information about patient flow, display the information as needed, analyze patient flow data, model the performance of the various health care subsystems within the facility, utilize actual patient flow information and associated histories in the design of simulations of patient flow, forecast the patient flow based on historical and simulated data, and simulate the effects of changes that modify health care systems, accordingly, to improve patient flow.

SUMMARY OF THE INVENTION

This invention consists of software-based decision support tools, which measure and analyze patient flow within and among health care facilities, as well as methods to model and measure patient flow. The decision support tools are readily customizable to a specific health care facility's characteristics and needs. Utilizing these tools, health care managers and executives may interpret patient flow data and improve patient flow in other critical related processes. The computer-implemented tools and processes of the present invention are made up of several parts.

First, a specific health care system, such as a hospital, is defined and characterized by its major component parts or departments. For example, a typical hospital incorporates a management and administration division to perform well-known personnel, accounting, data processing, and related management functions. In addition, a hospital is divided into a wide array of clinical departments: surgery, radiology, physical therapy, psychology, cardiology, urology, neurology, and emergency treatment. Utilizing these examples, it is possible to further subcategorize hospital departments. For example, the emergency room may be divided into subdivisions such as triage, trauma, acute care, cardiac care, obstetrics and gynecology, and administrative sub-departments such as patient intake and patient registration. The activities and processes performed in each of these subsystems can be modeled through sets of rules and algorithms, which quantify patient flow in, out, and through each subsystem.

Models created for and applicable to each of the above-described subsystems can initially be established based on a broad range of health care system experience in similar health care facilities, thereby creating a starting point, or generic model, providing an initial reasonable approximation of the actual performance of a typical sub-department, such as triage. The present invention, however, includes the ability to customize the generic model for a specific health care system, any department within that system, and any sub-department within any department.

In the method of the present invention, the mathematical models so created are complex, and accordingly, are implemented in computer code using a wide variety of commercially-available software tools.

The computer models so created form the framework within which data regarding patients and activities will be input and analyzed. The data utilized by the system is the same data that the health care facility collects and utilizes for individual patient management issues. For example, each patient's name, age, diagnosis, medications, treatment plan, location, test results, physicians, and schedule are stored in electronic form in a hospital database. In some systems, real-time patient data acquired through telemetry is also available for analysis and use by the invention. The invention contains software processes to link this patient data, as well as other hospital data, to the models associated with each component and subcomponent.

The invention further comprises processes to define various outputs from the computer model and to make those outputs available to hospital personnel in the form of electronic or printed displays and reports.

In addition to the foregoing, the present invention provides for the operation of the model utilizing theoretical data for purposes of simulating facility performance and end points based on theoretical events. In other words, the system can report and display data regarding actual performance and can also forecast performance based on theoretical data and events. The models for each subsystem can be easily changed to simulate the dynamics of any particular component or sub-component of the health care system.

The invention is designed to demonstrate the effects that changes to the actual healthcare system under study would have if for example, staffing is altered by type, number, or schedule; facility layout, service mix or workflows are changed; specialized treatment pathways are implemented; etc. Moreover, process changes that are thought to be best demonstrated practice can be simulated within a customized model. The effects of these alternatives can be parametrically shown over and against the "normal" functioning of the health care system.

The invention therefore readily accommodates a wide range of "what-if" scenarios in the health care environment. For example, the system can accurately forecast the effects of the influx of a large number of trauma patients to the emergency room based on a major accident or natural disaster (a relatively short temporal event), and just as easily forecast expected changes in hospital dynamics as a result of a developing influenza epidemic (a relatively long temporal event). Hospital administrators can theorize and measure the affects of personnel changes in component or sub-component departments on patient flow. Each individual model characteristic of each hospital component can be easily adjusted by the present invention to simulate an infinite variety of change variables. Utilizing this information, hospital administrators are better equipped to recognize significant changes in patient flow and modify performance of health care systems to thereby accommodate those changes and improve patient care. Hospital administrators can also easily select what changes should be made to their current operations based on the outcome of simulating alternative processes within their own system model.

DETAILED DESCRIPTION OF THE DRAWINGS

The description herein makes reference to the accompanying drawings wherein like referenced numerals refer to like parts throughout several views and wherein:

FIG. 4 is an example of the code utilized in the creation of the mathematical model for emulation of patient flow.

FIG. 8 is a typical computer output screen depicting selected data regarding patient flow in a typical health care environment.

FIG. 9 is a flow chart depicting the tuning of the modeling process.

DESCRIPTION OF THE PREFERRED EMBODIMENT

Figure 1:
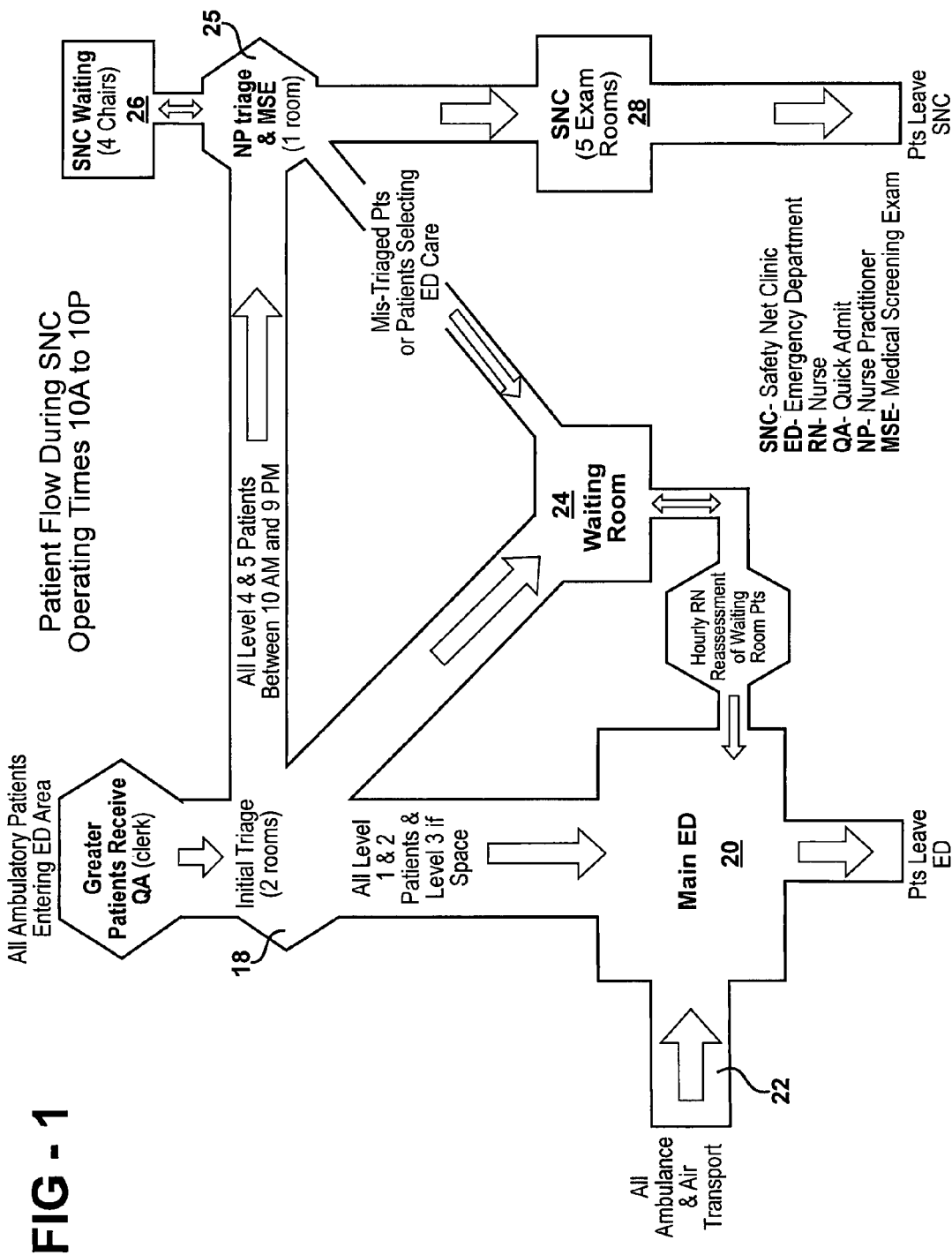
FIG. 1 is a flow chart depicting movement of patients through a typical hospital emergency department.

Referring to the drawings, the present invention will now be described in detail with reference to the disclosed embodiment.

With the understanding that the processes and methods of the present invention are broadly applicable to health care systems as a whole, and equally applicable to each department within the health care facility, the following description of the embodiment is directed to a typical and familiar component of a modern hospital, i.e., the emergency department, sometimes colloquially referred to as a "emergency room."

In reality, the emergency department of the modern hospital is no longer confined to a "single room," but constitutes a much larger physical complex, impressively equipped and staffed to meet a wide variety of emergency situations. Since the emergency department of today's hospital has taken over the functions of many primary care physician's offices, the department must provide a wide range of critical care services to an equally wide range of patient complaints ranging from the routine and mundane, such as a upper respiratory infection to the true emergency, e.g. a gunshot wound or a heart attack.

Figure 2:
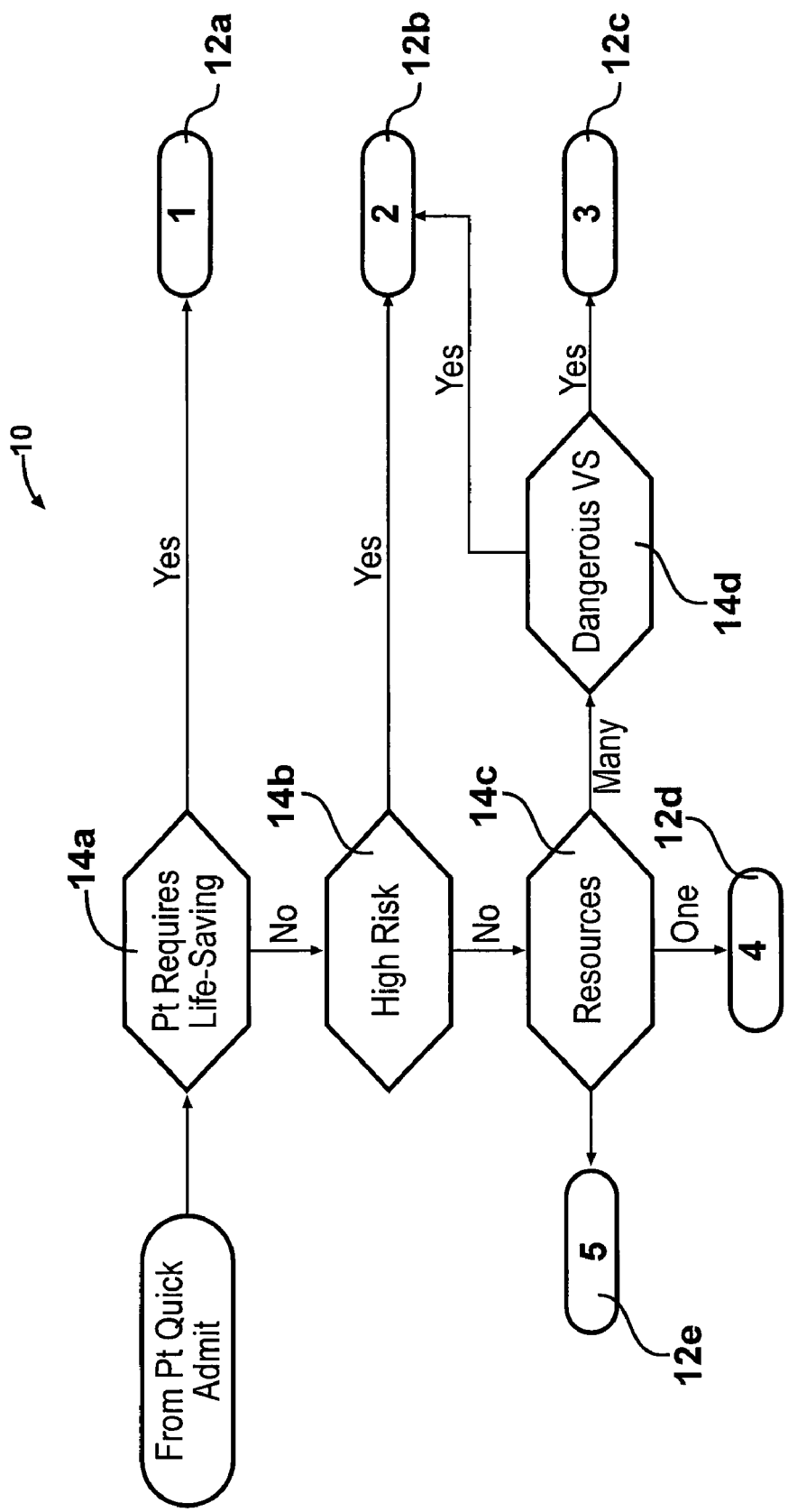
FIG. 2 is a flow chart depicting the numerical classification assigned to patients based on a patient's physical condition upon presentment of the patient to the emergency department of the health care facility.

Each health care facility has evolved its own set of rules and pathways for processing emergency department patients, of which FIG. 1 and FIG. 2 are typical. The present invention allows effective modeling, however, regardless of the rule sets and procedures in use, and is readily customizable to a wide range of health care delivery processes. Different mathematical models can be created as needed for different health care systems through the creation of different algorithms for those systems.

In FIG. 2, for example, the initial decision process regarding patient classification is depicted in flow chart form. In this example, a typical triage procedure 10 is depicted. It will be appreciated that such a triage procedure is merely one of several initial patient classification systems which are known and available for use in emergency departments. This particular rule set contemplates that an ambulatory patient entering the emergency department is first evaluated by one or more health care professionals and placed based on decision points 14a-14d, into one of five treatment categories 12a-12e. Those patients requiring immediate lifesaving procedures are placed in classification one. Patients who do not require immediate lifesaving procedures, but who are deemed to be at very high risk of physical deterioration or death are placed in classification two. Patients who are not considered to be at high risk are next evaluated in terms of the health care facilities available resources. Assuming the departments available resources are sufficient, patients are divided into two further classifications based on their current vital signs. Those patients exhibiting dangerous vital signs are placed in classification two, while those with normal vital signs are placed in classification three. If the emergency department's resources are limited, however, non-high risk patients are placed in classification four. In the situation where the emergency department has no available resources for treatment of non-high risk patients, such patients are placed in classification five.

Once the incoming patient has been appropriately classified, the patient's processing through the emergency department takes place, in the exemplary rule set, as depicted in FIG. 1. Once the initial triage 18 has been completed, level one and two patients (and level three patients if space is available), are immediately moved to the main emergency department 20 for treatment. The main emergency department 20 also acts as the input point 22 for patients delivered to the emergency department by ground or air ambulance, the assumption being that patients so arriving are either in a life threatening condition or are extremely high risk.

Patients classified at level three, in the event that immediate treatment in the emergency department is not available are routed to the main emergency department waiting room 24, where they are cycled into the main emergency department as space permits. Patients in the emergency department waiting room 24 are routinely monitored by a health care professional who will reassess the patient condition periodically.

All level four and five patients in the present example are moved to a secondary "safety net" triage section 25, where a secondary evaluation is performed. Misevaluated triage patients may then be transferred back to the main emergency department waiting room as necessary, whereas correctly evaluated patients may either be moved to either a secondary safety net waiting room 26 or a secondary safety net examination and treatment room 28. Once treatment has been completed in either the main emergency department or the secondary safety net department, the patients will leave those areas for further treatment or discharge.

Figure 3:
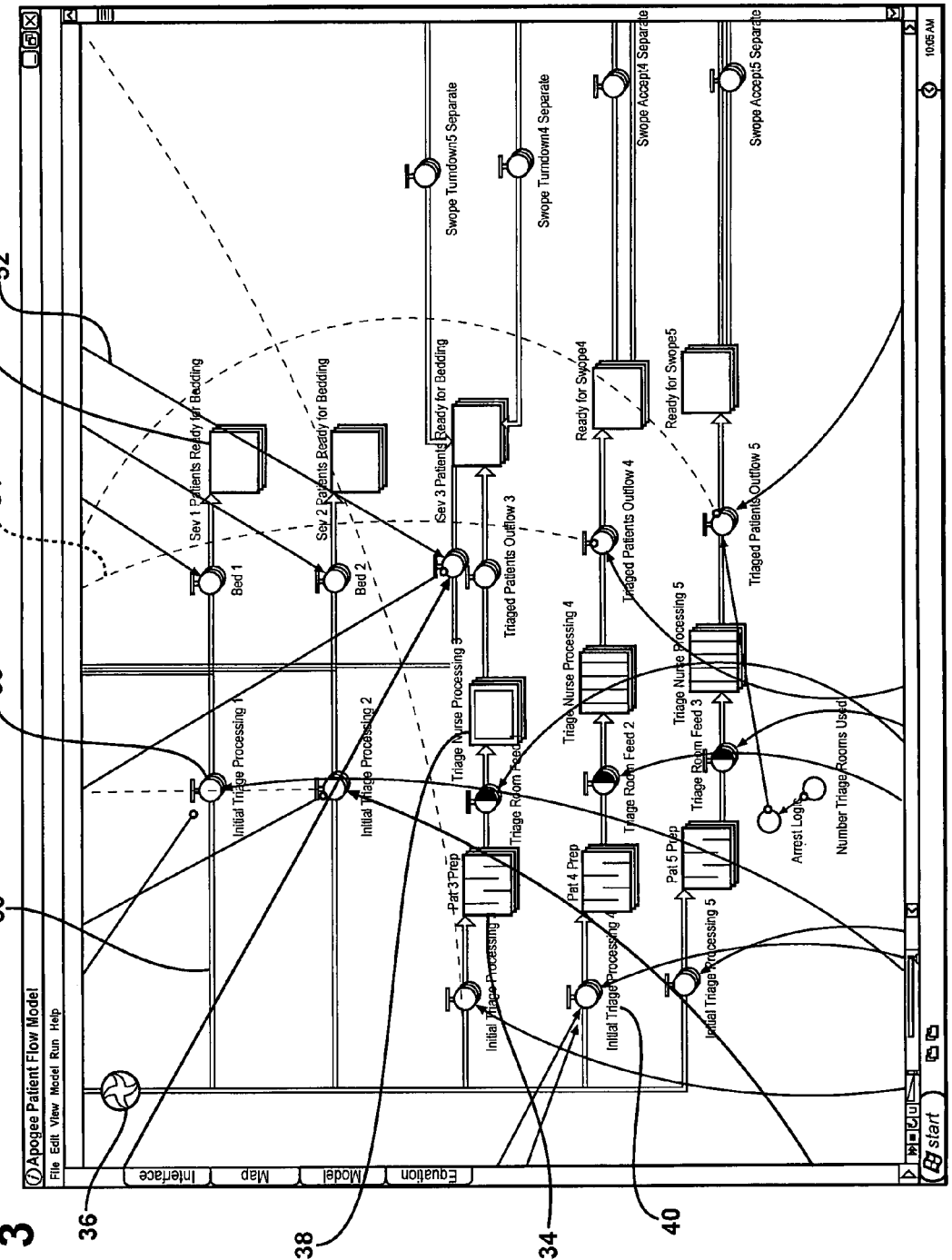
FIG. 3 is a visual representation in iThink format of a portion of one diagrammatic view of an exemplary section of a triage activity in a health care system.

With reference now to FIG. 3, the mathematical model for emulation of patient flow based on the above description will be better understood. FIG. 3 is a depiction of a portion of the patient flow through the emergency department as described in relation to FIG. 1. FIG. 3 will be recognized, by those skilled in the art, as a typical representation of a visual block diagram using a programming tool such as IThink, a well known computer application often used for business modeling. In the example of FIG. 3, numerous "valves" 30, "reservoirs" 32 and logical controls 34 appear and are represented by characteristic icons. Icon 36, in the stylized form of a pump, represents a variable source, in this case, a source of patients into a particular component of the emergency department. An array of "valves" 30, which may be, for example, one or more health care professionals who are controlling the quantity and direction of the patient flow throughout the department 15 is also presented. An array of reservoirs 32, represents areas in which patients may be held for varying lengths of time. Certain types of reservoirs 32 are represented by more specialized icons, such as icon 34, which represents an array of queue reservoirs, or icon 38 which represents an array of processing reservoirs.

It should be appreciated that FIG. 3 provides a visual representation of only a segment of the patient flow depicted in FIG. 1, depicting, in this example, a segment of the patient flow for patient classifications 1 through 5 through triage.

For example, in the "valve" step 40 designated "initial triage processing 4", a mathematical model is created for initial triage processing 4, followed by a mathematical model for queuing those patients and moving those patients for presentation to the triage room, controlling the flow of patients for triage nurse processing, and, in this example, transferring the patients to the secondary safety net department for further processing.

A sample mathematical model for a portion of this activity is depicted in the code outlined in FIG. 4. This code is generated automatically by the IThink application in response to the selection and placement of icons on the IThink visual programming window and by providing customized information for the functionality of each said icon in response to the functions to be performed at that step in the program. The first section of FIG. 4, for example, is the mathematical model which describes the functionality of the "ready for swope" icon array depicted in FIG. 3. The first line of the applicable code defines the differential equation which simulates the functionality of the block, while the remaining lines of code define the elements of the variables and the remaining logic which allow the model to function.

The software is used to create mathematical models for each activity, including patient inflow into the emergency department, multiple triage steps, waiting, treatment, transfer and discharge. In FIG. 3, the double lines 50 serve to designate paths of actual patient flow through the system, while the single lines 52 designate the flow of computer instructions between the individual mathematical models, the dotted lines 54 represent the flow of data.

Figure 5:
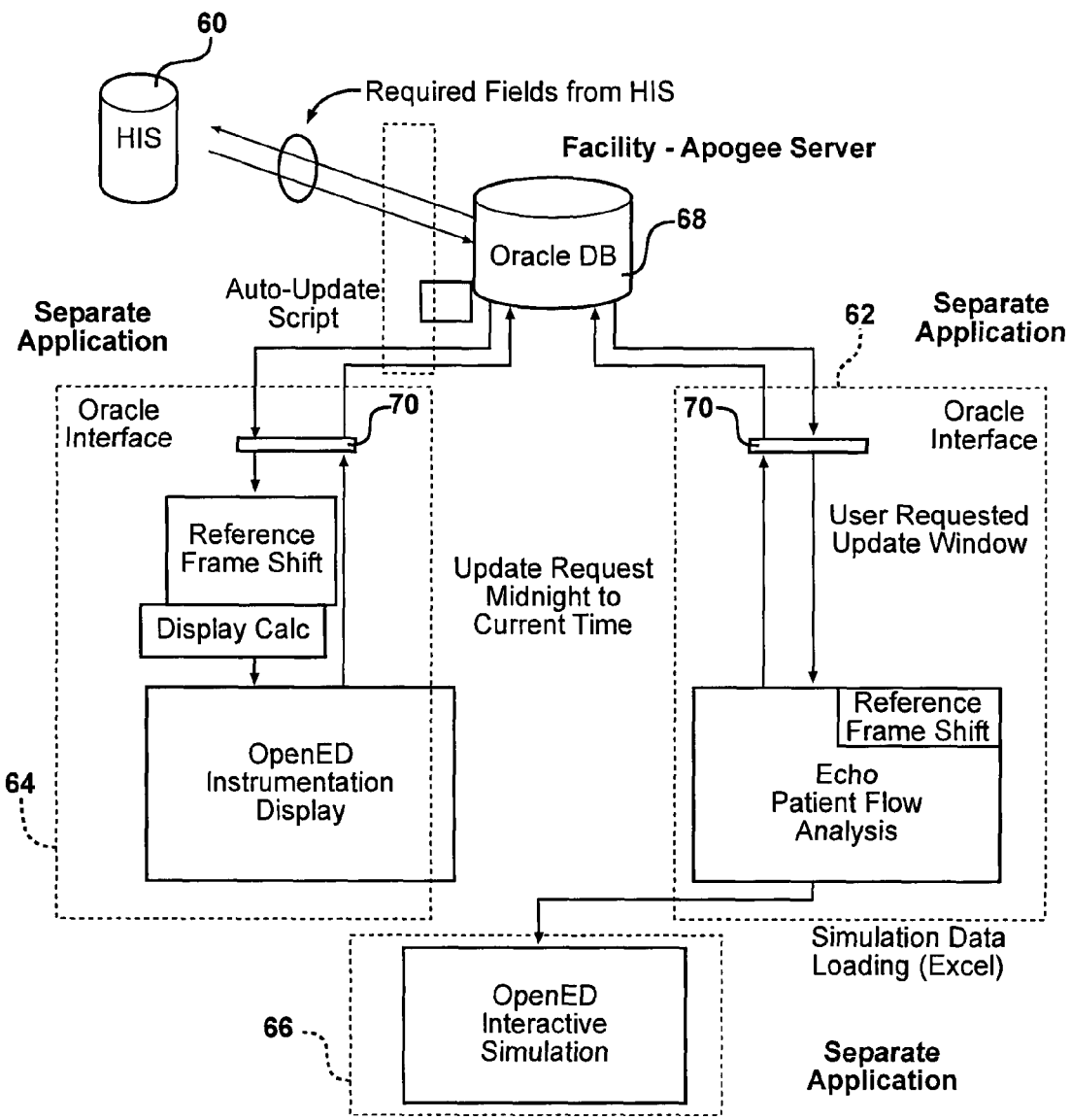
FIG. 5 is a flow chart depicting the interface between the three major applications which comprise the present invention, and the interface of the systems with the hospitals database.

In the present invention, the method interfaces with the hospital information system computer 60 as depicted in FIG. 5. The method of the present invention incorporates three separate but interconnected computer applications, (1) the programmable instrumentation interface 62, (2) the display and reports system 64 and (3) the interactive simulation application 66. Both the programmable instrumentation interface and the display and reports system 64 utilize information from the hospital information system computer 60. The interactive simulation application 66 communicates directly with the programmable instrumentation interface 62. In one embodiment of the invention, the interface between the programmable instrumentation interface 62 and the hospital information system 60, as well as the display and reports system 64 and the hospital information system 60 is achieved through the use of a separate server 68 utilizing Oracle database software to provide a buffer between the hospital information system 60 and the present invention. These interfaces 70 are achieved through the use of either a hardware or software server.

In the embodiment, the programmable instrumentation interface 62 application consists of a database and a coded set of instructions. It may be configured to run on a separate computer within the hospital infrastructure. Its proprietary instruction set uses SQL statements, HL-7 interpreters and other direct data transfers or transformations to generate a timed sampling of portions of designated hospital information systems to transform or manipulate data and store it in a form for later retrieval by the display system 64. The instrumentation interface 62 data storage window is configurable. A typical instrumentation interface data storage window is depicted herein as FIG. 7.

The display and reports system application, uses information stored by the programmable instrumentation interface. On request from the user, the application may extract data, transform and/or format data, and plot and display data regarding patient flow and hospital statistics for a selected time frame. The users have the ability to select any time interval within the storage capability of the data processing system via menu driven options. Information which may be displayed include enterprise level data such as average severity of illness or injury, department capacity, average process intervals and turn around times. The display and reports system also provides formatted data in the form of Microsoft Excel files for a specific day for use by the interactive simulation. As suggested by FIG. 8, this data can represent actual historical patient data, forecasted data (based on trend analysis) or synthetic patient data that would include stochastic input for simulation purposes. Data fed from the display and reports system can be utilized for analysis of patient load, and to project patient load for sometime period forward based on historic patient presentation patterns.

The third application in making up the system of the invention is the interactive simulation, which consists of patient throughput and flow models connected to a user interface and supporting equations for simulating different reactions to parametrically changing conditions. The interactive simulation interface provides connectivity to the complex patient throughput and flow models and adjustments. The interactive simulation provides graphical, tabular or computer based output derived from the manipulation of any of the vast number of model input variables. For instance, results of plotted include hospital occupancy percentages, number of patients in waiting room, acuity levels across specified time periods, admitted patient time series, discharge patient time history, fill and drain rates across any departments care intervals, and a variety of other parameters.

The patient throughput and flow models are built from differential equations, as above described, that represent the patient management processes. These models may be customized for different health care facilities utilizing specialized data from the facility to modify the equations. The models are interconnected to represent patient flow through the health care facility as above described. These models may be stored and recalled.

All three applications above described are highly configurable and may be readily modified to a particular health care facilities needs.

DETAILS OF THE OPERATIONS OF EACH OF THE APPLICATIONS

The Programmable Instrumentation Interface

A typical health care facility inputs, processes and stores vast amounts of data regarding each patient. This data is typically input by hospital personnel through the use of data entry devices such as computer terminals. Additional information regarding each patient may be input by wireless handheld devices such as personal digital assistants, by hospital monitoring equipment, and devices such as barcode readers and wireless telemetry systems. Data regarding each patient may be collected at some or all stages of the patients course of treatment in the health care facility, and as a result, the movement, diagnosis, treatment and location of each patient is the subject of continuous data inputs throughout the patients stay at the health care facility. Periodically, portions of this information may be summarized and displayed on tracking boards, such as those used in emergency departments. In addition to the foregoing, health care facilities maintain computer aided systems for room and bed management, and the health care facility may also maintain additional related databases of information regarding facilities and personnel. All of these systems are continuously updated with new data as conditions within the health care facility change. The variables associated with the health care facility operation are extremely dynamic. Nevertheless, patterns in the change and rate of change of these variables develop and are subject to analysis and forecast.

As above described, the programmable instrumentation interface extracts patient activity data from the health care facility database. Typically, the programmable instrumentation interface application is configured to run on a separate computer within the health care facility infrastructure. The programmable instrumentation interface samples pre-selected data from the health care facility information system on a timed basis. The programmable instrumentation interface therefore "senses" condition within the health care facility based on the above described database. This information is then continuously transmitted and available to hospital personnel for display on computer output devices, such as a video display terminals. A typical real time patient flow display is depicted in FIG. 8 it should be appreciated, however, that FIG. 8 is merely an example of one configuration of real time patient flow instrumentation available utilizing the present invention and that the video display of FIG. 8 is readily customizable according to the users demands.

In this fashion, the programmable instrumentation interface application provides to hospital personnel a "dashboard" showing the instantaneous patient flow situation, including the number of patients waiting to be seen, mean or average acuity of patient condition at triage current capacities and mean or average length of service, as well as admissions and discharges.

In addition, the timed samples of data extracted from the health care facility system are stored by the programmable instrumentation interface in a dedicated database for a later retrieval by the display and reports application. The length of time over which data is stored is fully customizable by the user, and set at a sufficient interval to ensure the availability of a meaningful sample of data sufficient to provide a valid sampling on which the remaining elements of the invention may operate. The application further contains the necessary software interface to allow effective communication between the programmable instrumentation interface application and the Oracle™ database into which the time sampling data above referred to will be stored.

The Display and Reports System Application

The display and reports application utilizes the sampled information above described as collected, transformed and stored by the programmable instrumentation interface. The display and reports system application is designed to extract this data, transform and/or format the data, and provide visual plots, displays and reports regarding patient flow and hospital statistics for a selected time frame. This display and reporting information can be formatted in a wide variety of formats, such as Microsoft Excel.

Figure 7:
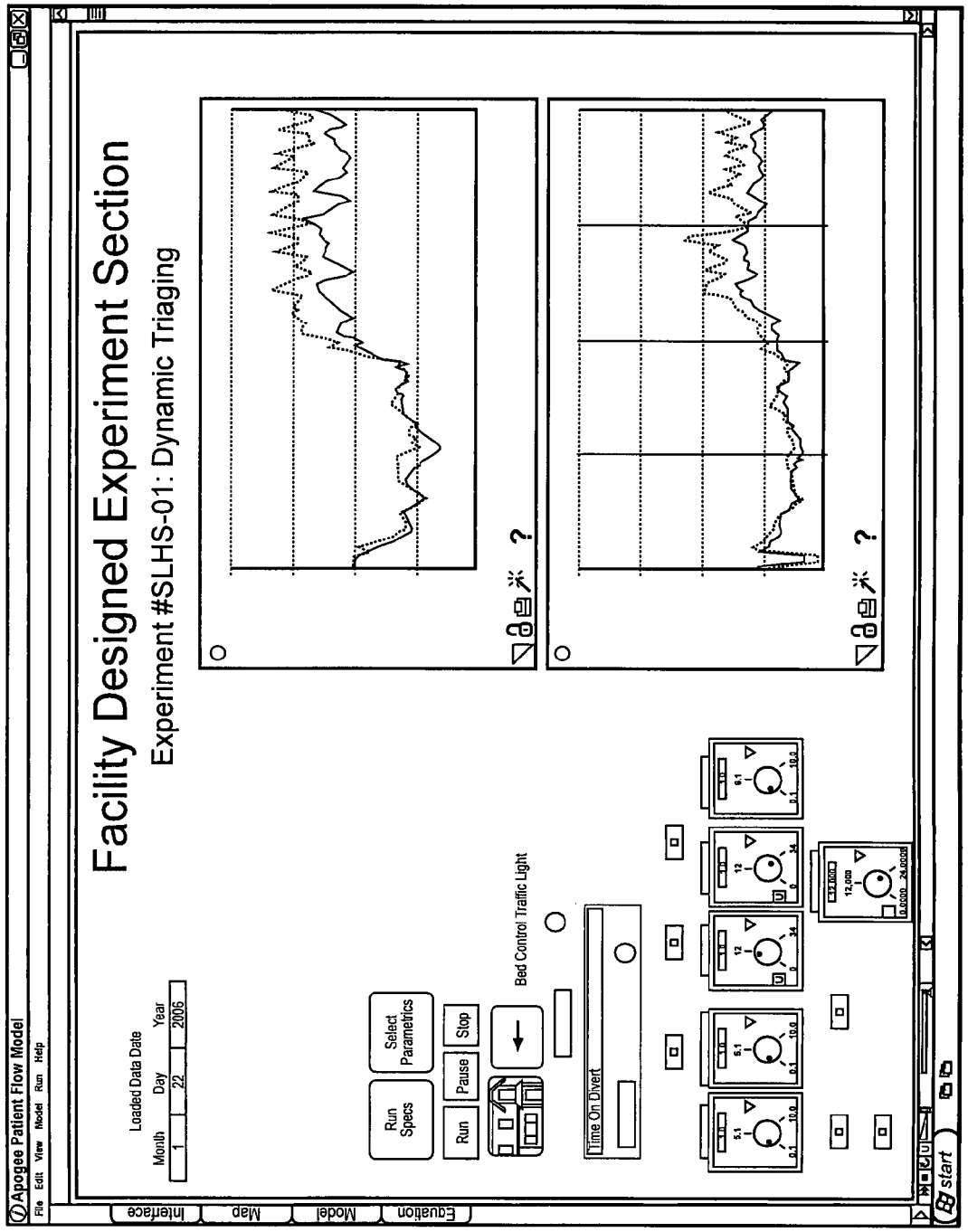
FIG. 7 is a typical computer input/output visual interface providing the ability to simulate potential conditions or process changes and measure those effects.

Whereas the real time patient flow information generated by the programmable instrumentation interface is not extensively interactive, the display and reports system is designed to provide a broader range of planning and management reporting functionality. Utilizing the display and reports system, the user, utilizing the computer terminal may design reports or graphs containing any number of a wide variety of data classifications stored in the Oracle™ database. The reports may be formatted to provide information for patient flow in hospital statistics during selected time periods. For example, if a hospital personnel wish to evaluate average severity of injury or illness in patients presented during a particular time range, the user may easily designate those classifications of data and time ranges and thereafter generate both tabular and graphical reports containing the required and requested data. A typical output so generated is depicted in FIG. 7.

Interactive Simulation Application

The third component of the present invention is the interactive simulation application. This application is basically a modeling system incorporating a user interface and associated mathematical processes for simulating reactions to changing conditions within the health care facility. The data on which the simulation application acts may be obtained from the Oracle™ database, as well as inputs from the user.

Figure 6:
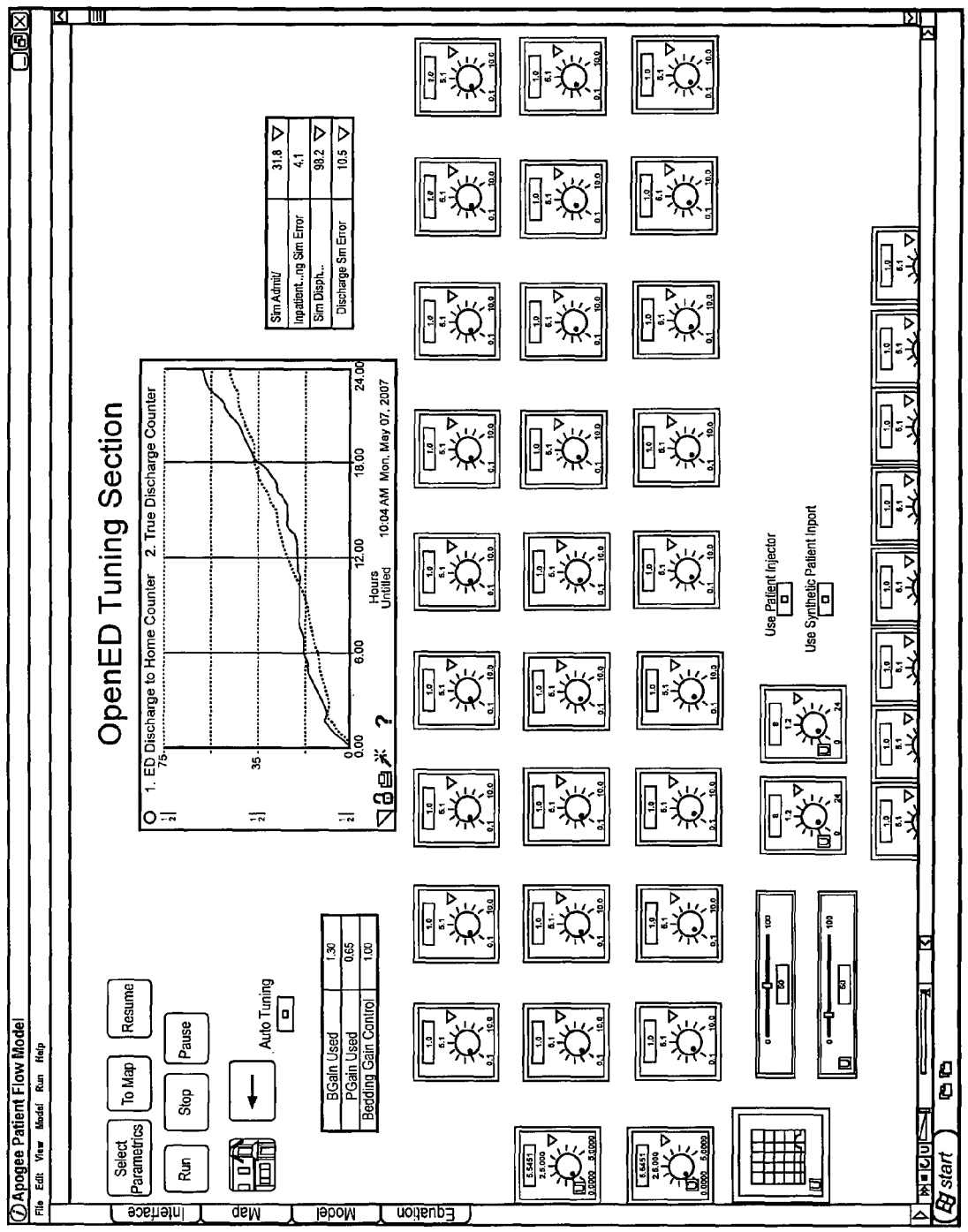
FIG. 6 is a depiction of the input/output screen utilized by the application to simulate changes in process variables.

An understanding of the performance of the interactive simulation application will best be understood by reference to FIG. 6, which is a representation of a computer screen which depicts both an actual and simulated discharge count from a typical emergency department.

Utilizing data maintained in the Oracle™ database, the interactive simulation application generates a graphical representation of true running total of patients discharged from a typical emergency department over a 24 hour period. For example, with reference to the upper trace as shown in the chart, after six hours of operation the actual number of patients discharged in the selected 24 hour time period was 17. With further reference to the graph, the recorded data from the health care facility indicates that at the end of the $18^{th}$ hour of the sample 24 hour period, a total of 35 patients had been discharged, and by the end of the 24 hour period, a total of 54 patients had been discharged. The graphical interface shown in FIG. 6 includes a number of graphical "dials", which permit the user to establish a wide variety of "what if" scenarios pertaining to treatment, waiting and other activities taking place within the facility. Here, for example, the user can alter the percentage of patients which are referred for particular testing, simulate additional or reduced patient load or modify a wide variety of parameters and thereby simulate changes in a health care environment, while viewing the net result of the alterations in environment on the variables selected.

The steps for creating the appropriate model for a particular sub-component of a sample health care facility department are next considered. Again, it will be appreciated that the following description pertaining to the modeling process is representative of an isolated portion of the process only, but the methodology is repeated throughout the process of constructing models for the various sub-components of the department and the functions therein performed.

The present example is based on FIG. 2, i.e., the classification of patients on presentation to the emergency department. This collection of steps, conventionally called "triage", is the process of sorting a random queue of arriving patients into sub-queues that have been classified by medical urgency, the demands the patients will place on the health care delivery system, thereby prioritizing the needs of the patient in the safest, most efficient fashion. Different health care facilities apply different classifications for triage, and conventional systems may classify patients into three, four or five grades of severity.

To gain an understanding of how a particular health care facility conducts the triage process, the next step of the process for creating the mathematical model involves a collection of the descriptive criteria applied to patient flow, patient condition and patient classification, including:

a. A description of how patients are directed to the entry point for the emergency department.
b. A description of how patients are uniquely identified within the specific health care system.
c. A description of each individual patient's chief complaint.
d. A description of urgency of condition based on variables such as pain scale, vital signs, estimate of immediate risk.
e. The method of assigning a numerical score or standardized label (e.g., critical, urgent, non-urgent).
f. The preparation of records
g. Procedures for tracking
h. Procedures for assigning places in a waiting queue All of the foregoing steps may involve accumulation of additional data including such variables as the actual physical constraints of the facility, written policies which detail business and clinical rules which impact patient flow, staffing constraints and accessibility of records.

Once all of the foregoing data has been gathered, this essentially "narrative" data is translated into a qualitative flow map which graphically depicts information about the clinical processes.

Next, the inventive method translates the clinical process into a stylized mechanical system utilizing the allegory of mechanical components such as pumps, reservoirs, queues and pipes. By using such a simulation, a mechanical system can be constructed with time-varying mathematical models which represent the processes.

Figure 10:
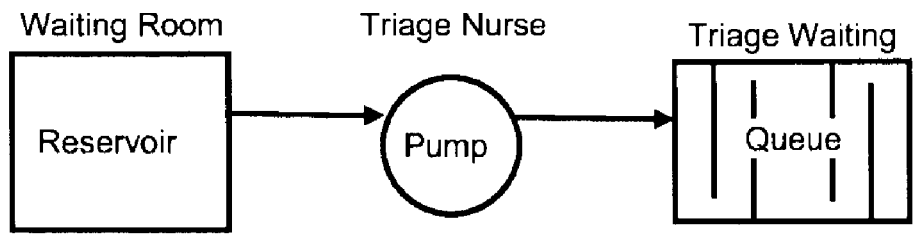
FIG. 10 is a simplified model depicting a clinical process using an allegory of mechanical components.

For example, a waiting room may be thought of as a reservoir, a triage nurse may be thought of as a pump, and a triage waiting area can be thought of as a queue as shown in FIG. 10, which is a simplified representation of the processes detailed in FIG. 3.

Using this analogy, actual data regarding the dynamics of flow of patients within and between each process is measured and translated into a set of general equations that characterize the flow. For example:

Triage Waiting=∫Pump Rate dt

By applying Runge-Kutta numerical integration methods, the integral can be approximated as:

Triage Waiting=Pump Rate*dt+Triage Wailing Initial Value, where dt is an integral time step.

These equations are further modified by bounding them in the model to adjust for a large number of factors that can affect the model, such as time of date, season of year, day of week, level of staffing, etc. Any factor which modifies or changes the expression of the core flow equations are referred to as a system characteristic or system variable. The relationships among these variables is determined and the numerical ranges over which they function are likewise determined. For example:

Triage Nurse can only see 1 patient at a time and can see 5 patients per hour (Triage Patient Rate) if Triage Waiting Queue is less than 3.

If Waiting Room>0 then if Triage Waiting old>3 then Triage Waiting new=Triage Waiting Old+Triage Patient Rate*dt else Triage Waiting New=Triage Waiting old To further subdivide patient flow parameters, flow management is altered using alternate characteristics for different patient acuity or sickness levels. These levels determine the speed by which the clinical staff manages the patient. The equations are replicated using array logic to emulate the clinical management of various patient types.

If Waiting Room (Severity 1)>0 then if Triage Waiting old (Severity 1)>3 then Triage Waiting new (Severity 1)=Triage Waiting Old (Severity 1)+Triage Patient Rate (Severity 1)*dt else Triage Waiting New (Severity 1)=Triage Waiting old (Severity 1)

If Waiting Room (Severity 2)>0 then if Triage Waiting old (Severity 2)>3 then Triage Waiting new (Severity 2)=Triage Waiting old (Severity 2)+Triage Patient Rate (Severity 2)*dt else Triage Waiting New (Severity 2)=Triage Waiting old (Severity 2)

Figure 11:
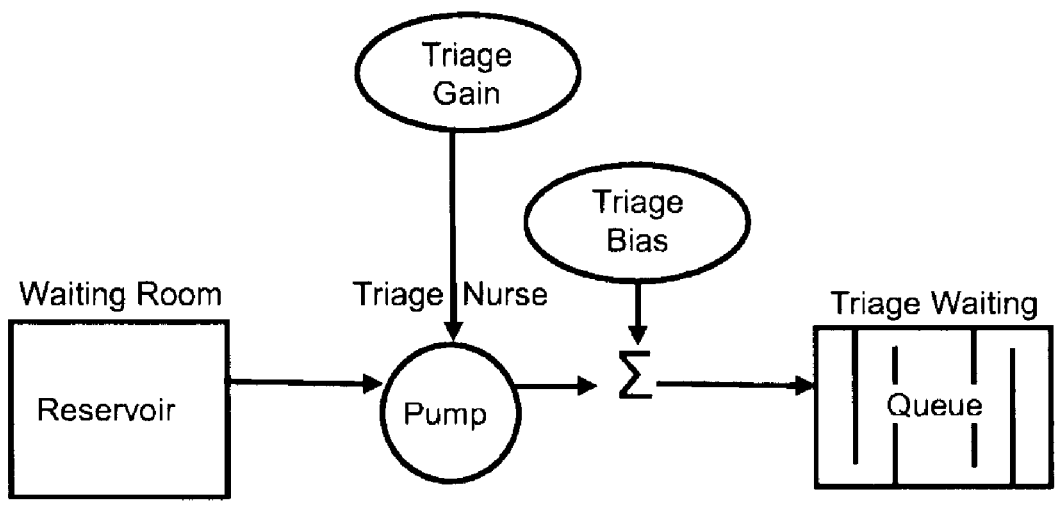
FIG. 11 is a refinement of the model of FIG. 10 incorporating gain and bias.

It will be appreciated that clinical processing of patients cannot be completely emulated and positively anticipated through mathematical modeling utilizing mechanical systems. The practicalities of treatment in health care facilities means that, as in any human process, there are unexpected events, such as delays, which occur during the treatment process, requiring the model to be "tuned" to more realistically emulate clinical events. A typical refinement of the modeling equations is depicted below, with reference also to FIG. 11:

If Waiting Room (Severity 1)>0 then if Triage Waiting old (Severity 1)<3 then Triage Waiting new (Severity 1)=Triage Waiting Old (Severity 1)+Triage Patient Rate (Severity 1)*dt*Triage Gain (Severity 1)+Triage Bias (Severity 1) else Triage Waiting New (Severity 1)=Triage Waiting old (Severity 1)

It will also be appreciated that the creation of the model for a health care facility department, such as an emergency department, will result in the creation of a large number of mathematical models and associated variables. All sub-systems within the larger patient flow system in a health care environment are inter-related and affect each other's performance. The output of one system is the input to the next system. To provide proper emulation of this cascading set of systems, all sub-systems are connected together to provide discrete flow events from system input to output. Each mechanical equivalent is provided with characteristics, gains and losses to properly emulate the sub-section flow.

Once the underlying equations and variables have been completed as above-described, the various mathematical relationships are translated into computer code.

The Runge-Kutta integration and combining logic to manage synthetic patient flow within the simulation is converted to computer code for processing. Computer code requires complete detailing of all possible variations for the mathematical algorithm. FIG. 4 is an example of the code utilized for a portion of the triage section of a typical emergency department model.

The Runge-Kutta numerical integration method uses the result of these equations to load the previous value for the integration cycle setup to loop every dt until the end of the specified time period (e.g., day).

As shown in FIG. 9, the simulation models are fed to the hospital information 60 system to transfer actual patient arrival times and severity scores to the model for processing a specific day. Along with the patient arrival information, sampled tuning data is collected to compare the results of the simulation with the day's events. The resultant error from the model is fed hack through adjusting algorithms to provide better tuning data for gain and bias adjustment valves.

Patient arrival model 100, triage model 102, bedding model 104, treatment model 106, discharge model 108, exit model 110 may all be modified, based on measured simulation error, by application of gains and biases 112.

What is claimed is:

1. A computer implemented method for displaying, analyzing, simulating and optimizing the flow of a population of patients in a health care facility comprising a computer performing the steps of:
   recording data in electronically accessible form, the data pertaining to the movement and location of each patient of the population of patients at a plurality of locations within said facility, the plurality of locations including at least one treatment location and at least one queuing location;
   generating patient flow statistics describing the movement of said population of patients within said facility based on said data;
   creating a mathematical model to represent patient treatment at said treatment locations and patient transit between said treatment locations and said queuing locations based on said patient flow statistics, the mathematical model including at least one differential equation representing a treatment rate at said treatment location based on said patient flow statistics and at least one differential equation representing an arrival rate at said treatment location based on the treatment rate and the patient flow statistics for said treatment location;
   selecting theoretical data regarding at least one of patient treatment or patient transit in said facility;
   applying said theoretical data to said mathematical model and
   generating theoretical patient population flow statistics by said application of said theoretical data.

2. The method of claim 1, wherein the mathematical model further represents at least one of patient treatment or patient transit at a second location of the plurality of locations within said facility based on said patient flow statistics, the mathematical model describing at least one operating characteristic of the second location that is dependent upon at least one operating characteristic of the first location.

3. An apparatus for displaying, analyzing, simulating and optimizing the flow of a population of patients in a health care system comprising:
   a software database containing data pertaining to the movement and location of each patient entering said system at a plurality of locations within said facility, the plurality of locations including at least one treatment location and at least one queuing location;
   a processor;
   a computer program implemented by the processor for selectively retrieving said data;
   a computer program implemented by the processor for generating patient population flow statistics based on said data;
   computer software implemented by the processor for the creation of a mathematical model to represent patient treatment at said treatment locations and patient transit between said treatment locations and said queuing locations utilizing said data, the mathematical model including at least one differential equation representing a treatment rate at said treatment location based on said patient flow statistics and at least one differential equation representing an arrival rate at said treatment location based on the treatment rate and the patient flow statistics for said treatment location;
   a computer program implemented by the processor for processing theoretical data regarding at least one of patient treatment or patient transit;

computer software implemented by the processor for applying said theoretical data to said mathematical model; and a computer program implemented by the processor for generating theoretical patient population flow statistics based on said data.

4. A computer implemented method for displaying, analyzing, simulating and optimizing the flow of a population of patients in a healthcare facility, comprising a computer performing the steps of:

recording data pertaining to the movement and location of each patient of the population of patients at a plurality of locations within said facility, the plurality of locations including at least one treatment location and at least one queuing location;

generating patient flow statistics describing the movement of said population of patients at said plurality of locations within said facility based on said data; and creating a mathematical model to represent patient treatment at said treatment locations and patient transit between said treatment locations and said queuing locations, the mathematical model including at least one differential equation representing a treatment rate at said treatment location based on said patient flow statistics and at least one differential equation representing an arrival rate at said treatment location based on the treatment rate and the patient flow statistics for said treatment location.

5. The method of claim 4, further comprising:

selecting theoretical data regarding at least one of patient treatment or patient transit in said facility;

applying said theoretical data to said mathematical model; and generating theoretical patient population flow statistics by application of said theoretical data.

6. The method of claim 4, further comprising:

conducting a simulation using said mathematical model;

comparing the results of said simulation to said data, wherein the data corresponds to the simulation;

calculating correction factors to conform the results of the simulation to the data; and applying the correction factors to the mathematical model.

* * * * *